United States Patent
Hernandez (10) Patent No.: US 11,747,313 B2
(45) Date of Patent: Sep. 5, 2023

(54) METHODS AND SYSTEMS FOR DETECTION OF VEHICLE OCCUPANCY

(71) Applicant: Monica Hernandez, Harbor City, CA (US)

(72) Inventor: Monica Hernandez, Harbor City, CA (US)

( * ) Notice: Subject to any disclaimer, the term of this patent is extended or adjusted under 35 U.S.C. 154(b) by 0 days.

(21) Appl. No.: 16/202,368

(22) Filed: Nov. 28, 2018

(65) Prior Publication Data

US 2020/0062080 A1 Feb. 27, 2020

Related U.S. Application Data

(60) Provisional application No. 62/721,141, filed on Aug. 22, 2018, provisional application No. 62/721,190, filed on Aug. 22, 2018.

(51) Int. Cl.
| | |
|---|---|
| *G01N 33/00* | (2006.01) |
| *B60H 1/00* | (2006.01) |
| *B60Q 5/00* | (2006.01) |
| *B60Q 1/52* | (2006.01) |
| *E05F 15/73* | (2015.01) |
| *B60N 2/00* | (2006.01) |
| *B60Q 1/50* | (2006.01) |
| *B60R 22/48* | (2006.01) |

(52) U.S. Cl.
CPC ....... *G01N 33/004* (2013.01); *B60H 1/00964* (2013.01); *B60N 2/002* (2013.01); *B60Q 1/52* (2013.01); *B60Q 1/544* (2022.05); *B60Q 5/005* (2013.01); *E05F 15/73* (2015.01); *B60R 22/48* (2013.01); *B60R 2022/4816* (2013.01); *E05Y 2900/55* (2013.01)

(58) Field of Classification Search
None
See application file for complete search history.

(56) References Cited

U.S. PATENT DOCUMENTS

| | | | | |
|---|---|---|---|---|
| 5,333,703 | A * | 8/1994 | James | F02D 17/04 |
| | | | | 454/75 |
| 9,227,484 | B1 * | 1/2016 | Justice | B60N 2/002 |
| 9,845,050 | B1 * | 12/2017 | Garza | G08B 21/0205 |
| 9,998,899 | B1 * | 6/2018 | Tannenbaum | G08B 21/0269 |
| 10,115,029 | B1 * | 10/2018 | Day | G06K 9/00832 |
| 2002/0161501 | A1 * | 10/2002 | Dulin | B06B 1/0215 |
| | | | | 701/45 |

(Continued)

*Primary Examiner* — Peter D Nolan
*Assistant Examiner* — Michael F Whalen
(74) *Attorney, Agent, or Firm* — Gearhart Law, LLC; David Postolski (57) ABSTRACT

Disclosed herein are system, method, and computer program product embodiments for detecting, alerting, and acting to prevent unattended vehicle deaths. An embodiment operates by receiving one or more signals from one or more presence sensors in a vehicle and analyzing the signals to detect the presence of a person or animal inside the vehicle. The system further receives one or more signals from one or more environment sensors on the vehicle and analyzes the signals to detect a dangerous environmental condition. If the system determines that both the presence of a person or animal has been detected inside the vehicle and a dangerous environmental condition has been detected, it activates one or more vehicle systems that mitigate the dangerous environmental condition and sends an alert to one or more predetermined recipients.

5 Claims, 3 Drawing Sheets

(56) References Cited

U.S. PATENT DOCUMENTS

| | | | | |
|---|---|---|---|---|
| 2005/0212681 | A1* | 9/2005 | Dzurko | G08B 21/14 |
| | | | | 340/632 |
| 2008/0117079 | A1* | 5/2008 | Hassan | B60R 25/045 |
| | | | | 340/901 |
| 2012/0310547 | A1* | 12/2012 | Cristoforo | G01N 33/0073 |
| | | | | 702/24 |
| 2015/0130604 | A1* | 5/2015 | Gomez Collazo | B60N 2/002 |
| | | | | 340/457 |
| 2016/0053699 | A1* | 2/2016 | Ozkan | F02D 41/042 |
| | | | | 701/112 |
| 2016/0075296 | A1* | 3/2016 | Alderman | G08G 1/127 |
| | | | | 340/989 |
| 2016/0200168 | A1* | 7/2016 | Boyer | H04R 19/04 |
| | | | | 701/45 |
| 2017/0158186 | A1* | 6/2017 | Soifer | B60W 10/30 |
| 2017/0318135 | A1* | 11/2017 | Han | G08B 21/14 |
| 2018/0025604 | A1* | 1/2018 | Protopsaltis | G08B 21/0205 |
| | | | | 340/457 |
| 2018/0053390 | A1* | 2/2018 | Morris | B60Q 9/00 |
| 2018/0056814 | A1* | 3/2018 | Tanyi | B60N 2/002 |
| 2018/0056988 | A1* | 3/2018 | Heil, Jr. | E05F 15/70 |
| 2018/0126950 | A1* | 5/2018 | Alderman | B60Q 1/50 |
| 2018/0197029 | A1* | 7/2018 | Ali | E05F 15/74 |
| 2018/0370431 | A1* | 12/2018 | Wincek | G01V 3/088 |
| 2019/0077217 | A1* | 3/2019 | Yu | B60H 1/0073 |
| 2019/0088104 | A1* | 3/2019 | Crewe | G08B 21/22 |
| 2019/0139386 | A1* | 5/2019 | Arinze | G08B 21/02 |
| 2019/0193590 | A1* | 6/2019 | Labombarda | G08B 21/22 |
| 2019/0215672 | A1* | 7/2019 | Orris | H04W 4/80 |

* cited by examiner

METHODS AND SYSTEMS FOR DETECTION OF VEHICLE OCCUPANCY

This application claims priority from U.S. Provisional Application No. 62/721,141 filed on 22 Aug. 2018 and U.S. Provisional Application No. 62/721,190 filed on 22 Aug. 2018, which are herein incorporated by reference in their entirety for all purposes.

BACKGROUND

Technical Field

Embodiments generally relate to computerized automobile sensors and controls, and in particular to systems and methods to prevent unattended vehicle deaths using sensors and wireless communications.

Background

"Hot car deaths" are a colloquial term to refer to deaths of persons (typically children or special needs individuals) or pets caused by heatstroke or hyperthermia due to being left alone in a car for a long time. A typical scenario involves a parent leaving an infant inside a car under the sun and forgetting about the child, returning many hours later to find the child has died of heatstroke. According to some estimates, an average of 37 children die each year in unattended vehicles.

While some technological solutions have been proposed and implemented to prevent these incidents, none have been able to provide a reliable system that mitigates the chances of death by detecting, alerting and acting appropriately based on the circumstances.

SUMMARY

Disclosed herein are system, method, and computer program product embodiments for detecting, alerting, and acting to prevent unattended vehicle deaths. An embodiment operates by receiving one or more signals from one or more presence sensors in a vehicle and analyzing the signals to detect the presence of a person or animal inside the vehicle. The system further receives one or more signals from one or more environment sensors on the vehicle and analyzes the signals to detect a dangerous environmental condition. If the system determines that both the presence of a person or animal has been detected inside the vehicle and a dangerous environmental condition has been detected, it activates one or more vehicle systems that mitigate the dangerous environmental condition and sends an alert to one or more predetermined recipients.

The embodiments disclosed above are only examples, and the scope of this disclosure is not limited to them. Particular embodiments may include all, some, or none of the components, elements, features, functions, operations, or steps of the embodiments disclosed above. Embodiments according to the invention are in particular disclosed in the attached claims directed to a method, a storage medium, a system and a computer program product, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

The accompanying drawings are incorporated herein and form a part of the specification.

DETAILED DESCRIPTION

Provided herein are system, method and/or computer program product embodiments, and/or combinations and sub-combinations thereof, for detecting, alerting, and acting to prevent unattended vehicle deaths. Embodiments include an integrated vehicle occupancy system that relies on the vehicle's on-board computer, the computer connected to a suite of sensors common in modern vehicles in addition to other sensors embedded within the vehicle's structure. The system can use sensors to detect that a person or animal has been left unattended inside the vehicle and that conditions inside the vehicle are dangerous (e.g., the cabin is very hot because the car has been left in the sun). The system can then issue alerts and/or take corrective actions to mitigate the dangerous conditions.

Figure 1:
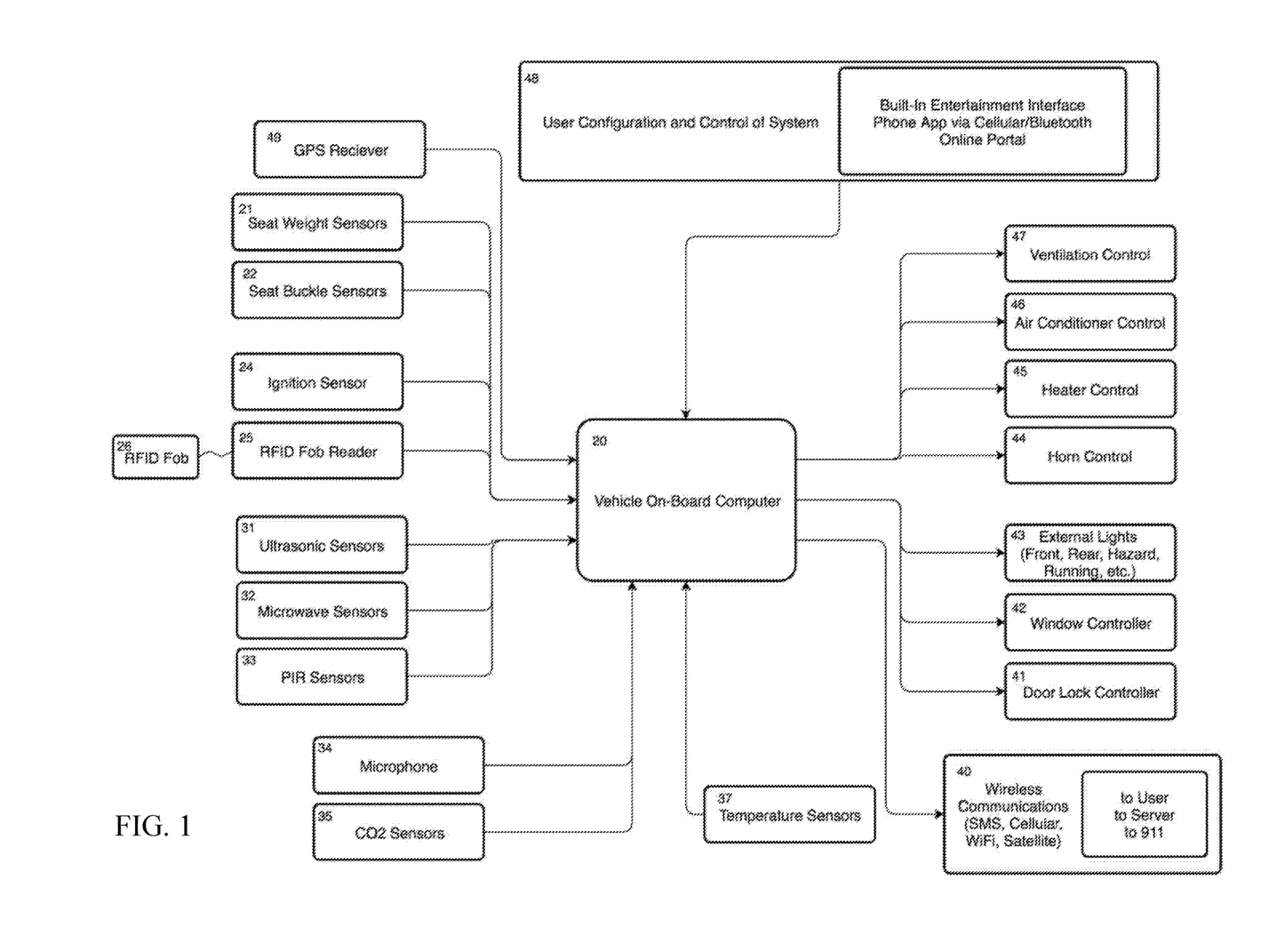
FIG. 1 shows a system diagram for an unattended vehicle death prevention system, according to an example embodiment.

FIG. 1 shows a system diagram for an unattended vehicle death prevention system 100, according to an example embodiment. System 100 includes a vehicle on-board computer 20 which executes software code for obtaining data from various vehicle sensors and controlling vehicle components. The system may be powered through the vehicle's alternator and 12 v battery. FIG. 1 shows on-board computer 20 receives input from one or more presence sensors. As used herein, a presence sensor is a sensor that can be used to detect when a person or animal is present in a vehicle. As an example, ultrasonic sensors 31, microwave sensors 32, passive infrared sensors 33, seat weight sensors 21, seat buckle sensors 22, microphone 34, and carbon dioxide sensors 35 can be presence sensors. Presence sensors may be positioned inside or around the vehicle. Computer 20 may analyze signals from any combination of these sensors to detect if a person or animal is inside the vehicle. As an example, an ultrasonic sensor 31 may be aimed towards a location in the car where a child passenger typically sits, e.g., the back seat. Ultrasonic sensors measure the distance to an object using ultrasonic sound waves. Computer 20 may calibrate the ultrasonic sensor to determine the distance read between the sensor and the empty seat. Computer 20 may then periodically read the signal from the ultrasonic sensor and determine that the distance read by the sensor is less than the predetermined empty-seat-distance, and thus determine that a person or animal is likely in the seat. Microwave sensors 32 may be used in a similar fashion.

Computer 20 may continuously receive and evaluate readings from various sensors to corroborate whether a person or animal is actually in the car and not another object. For example, a passive infrared sensor 32 may be used to distinguish between inanimate objects and a living thing, e.g., person or animal. A passive infrared sensor is an electronic sensor that measures infrared (IR) light radiating from objects in its field of view, and are often used in motion detectors.

In other examples, computer 20 may analyze microphone 34 signals to detect particular noises, e.g., a child crying, talking, dog bark, moving or tapping noises, etc. Seat weight sensors 21 may detect a particular weight corresponding to a human or animal, while seat belt buckle sensor can detect that a seat belt is still 22 buckled. Carbon dioxide sensors 35 may detect an increase in carbon dioxide inside the vehicle, indicating a person may be inside the car with the windows closed. While particular presence sensors and presence detection methods are described herein, this disclosure contemplates any suitable presence sensors and presence detection methods.

Computer 20 may further receive input from one or more environment sensors. As used herein, an environment sensor is a sensor that can be used detect particular environmental conditions in or around the vehicle. As an example, temperature sensors 37, carbon dioxide sensor 35, or toxic or hazardous gas sensors (e.g., carbon monoxide sensors, smoke sensors, car exhaust fumes sensor, etc.) can be environment sensors. Computer 20 may analyze the signals from environment sensors to detect dangerous or hazardous environmental condition. As an example, computer 20 may read a temperature from a temperature sensor 37 and determine that the temperature inside a vehicle is dangerously high or low. Other sensors may monitor for toxic or hazardous gases at dangerous levels, such as, carbon dioxide, carbon monoxide, car exhaust fumes, etc. As such, computer 20 may be able to detect to dangerous conditions other than hot or cold cars, such as a gas-powered vehicle that has been left running in a confined space and poses a risk of intoxication for occupants.

Computer 20 can control various systems in the vehicle in order to take action after detecting a person or animal is inside the vehicle while the conditions inside the vehicle are unsafe. For example, computer 20 may communicate with a door lock controller 41, window controller 42, external lights control 43, vehicle horn control 44, heater control 45, air conditioner control 46 and/or ventilation control 47 to perform appropriate actions to mitigate dangerous conditions or alert nearby persons of the dangerous situation. As an example, if a child has been left unattended in a hot vehicle, computer 20 may turn on the air conditioning to lower the temperature inside the vehicle. Computer 20 may turn on the vehicle heater if a child has been left in a vehicle at very cold temperatures. The system may unlock doors, open windows, flash lights, and sound the horn to alert any nearby persons to the situation and allow them to help. Computer 20 may thus monitor conditions in the vehicle and perform appropriate actions to mitigate risks.

Computer 20 may further be connected to a wireless communications system 40, and may control it to transmit notifications, messages, or phone calls based on detecting dangerous situations as explained above. Wireless communications system 40 may include cellular antennas, satellite system, Wi-Fi, etc. As example, computer 20 may call or message emergency services (e.g., 911) or numbers from a predefined list of contacts to alert of the dangerous situation.

Computer 20 may receive configuration information from a user through a user interface 48 in communication with computer 20. The interface may be provided through a built-in entertainment system (e.g., infotainment system) in the vehicle, a mobile app, a web interface, etc. As an example, a built-in infotainment system in the vehicle may provide menus and commands to activate and configure computer 20 for detecting, alerting, and acting to prevent unattended vehicle deaths, including entering emergency contacts information and configuring what actions to perform during a detected emergency. Interface 48 may thus be used to customize alert recipients and alert messages, configure and test the system, and view system status information.

Figure 2:
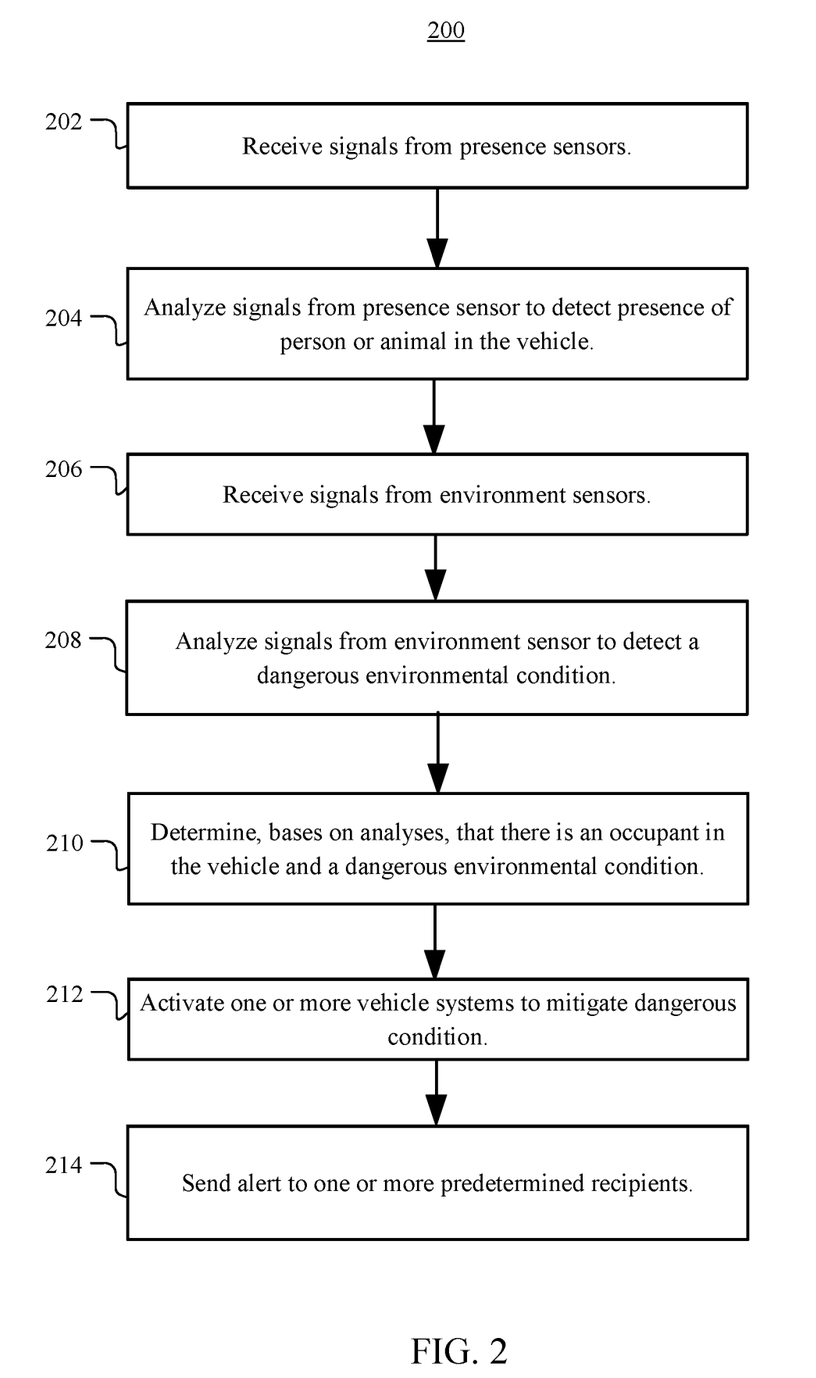
FIG. 2 is flowchart for a method of detecting, alerting, and acting to prevent unattended vehicle deaths, according to an example embodiment.

FIG. 2 is a flowchart for a method 200 of for detecting, alerting, and acting to prevent unattended vehicle deaths, according to particular embodiments. Method 200 can be performed by processing logic that can comprise hardware (e.g., circuitry, dedicated logic, programmable logic, microcode, etc.), software (e.g., instructions run on a processing device), or a combination thereof. In particular embodiments, computer 20 may initiate method 200 upon determining that a vehicle is unattended. Computer 20 may determine that a vehicle is unattended based on one or more conditions, such as, for example, detecting that the vehicle's RFID fob reader 25 does not detect the presence of key fob 26, detecting that the vehicle's ignition is off, when the driver's seat weight and/or seat belt buckle indicate that the driver seat is unoccupied, etc.

At step 202, computer 20 receives one or more signals from one or more presence sensors in a vehicle. At step 204, computer 20 analyzes the one or more signals to detect the presence of a person or animal in the vehicle. As an example, computer 20 may continuously or repeatedly analyze the signals from the presence sensors (e.g., ultrasonic, microwave, infrared sensors, etc.). The analysis may involve, for example, comparing the signal reading to a previously calibrated value corresponding to an empty seat, thus indicating that something is occupying the seat. In an example, the analysis may involve determining whether the signal changes in a particular manner, thus detecting movement and indicating that a person or animal is occupying the vehicle.

In particular embodiments, presence sensors may monitor the outside of the vehicle, and analyzing for presence may include maintaining a count of the number of persons or animals that have entered and exited the vehicle. As an example, computer 20 may analyze signals to determine that two persons entered the vehicle, and later one person left. As such, computer 20 may determine that a person is present in the vehicle.

In particular embodiments, computer 20 may analyze carbon dioxide levels in the vehicle to determine whether a person is present. As an example, computer 20 may determine that the vehicle windows are open and activate the window controls to close the windows. Computer 20 may then continuously monitor the carbon dioxide sensor readings over time to determine if the levels of carbon dioxide inside the vehicle are increasing. An increasing level of carbon dioxide would indicate that a person or animal is inside the vehicle, as their breathing would produce carbon dioxide. While measuring the carbon dioxide, computer 20 may also monitor the temperature inside the vehicle to ensure that the occupants remain safe. Once the measurements have been taken, computer 20 may re-open the windows to reduce the threat of heat build-up in the vehicle.

At step 206, computer 20 receives one or more signals from one or more environment sensors on the vehicle. At step 208, computer 20 analyzes the one or more signals from the environment sensors to detect a dangerous environmental condition. Computer 20 may continuously or repeatedly analyze the signals from the presence sensors to detect dangerous conditions. As an example, computer 20 may continuously read the temperature from temperature sensor 37 to determine if the temperature inside the vehicle is outside of a preconfigured safe range.

At step 210, computer 20 determines whether both the presence of a person or animal inside the vehicle and a dangerous environmental condition have been detected, based on the analyses of steps 204 and 208. If so, computer 20 performs actions as specified in the system configuration. At step 212, computer 20 activates one or more vehicle systems that mitigate the dangerous environmental condition. The actions taken may be configured by a user through interface 48. As an example, computer 20 may turn on the car ignition and activate the air conditioning if the vehicle is overheated, or close the windows and turn on the heater if the vehicle is at dangerously cold temperatures. In an example, computer 20 may detect unsafe levels of toxic gases inside the vehicle (e.g., carbon dioxide, carbon monoxide, car fumes, etc.) and may activate the vehicle's ventilation system in response. In particular embodiments, the system may continuously monitor conditions in the vehicle and adjust actions accordingly. As an example, the air conditioning may be activated until the temperature returns to a safe level and then adjusted to maintain the safe temperature. In an example, computer 20 activates car systems to alert nearby persons or passers-by of the emergency, such as activating a car alarm, car horn, flashing lights, unlocking doors, etc.

There may be situations in which taking certain actions may be unsafe. As an example, if the vehicle is a gas-powered vehicle and it is in a confined space, turning on the air conditioning may cause car fumes to enter the vehicle. Computer 20 may take certain preventive measures to determine if it is safe to perform a mitigating action. In particular embodiments, computer 20 may analyze sensor readings to determine if the vehicle is in a confined space. In an example, the computer 20 may turn on the ignition and partially or completely open windows and analyze readings from dangerous gas sensors to determine if there is an increase in dangerous gases (e.g., carbon monoxide, car fumes, etc.). If the gas measurements increase above predetermined rate or concentration computer 20 determines the vehicle is likely in a confined space without proper ventilation, and in response turns off the ignition to avoid generating further toxic fumes. In an overheated vehicle scenario, computer 20 may open the vehicle windows and turn on the ventilation system without starting the vehicle engine. In a cold vehicle scenario, computer 20 may close the windows.

In particular embodiments, computer 20 may further receive signals from surroundings sensors. As used herein, surrounding sensors are sensors that monitor areas around the vehicle. As an example, surrounding sensors may be sonar, radar, LiDAR, cameras, etc., such as proximity sensors used for automated driving, lane changing, parking, etc. Computer 20 may use surrounding sensors to determine if the vehicle is in an enclosed space before performing other mitigating actions, as explained above.

At step 214, computer 20 sends an alert to one or more predetermined recipients. The predetermined recipients may be configured by a user through user interface 48, e.g., contacts, emergency response, 911, etc. The type of alert may also be configured, such as, for example, SMS text messages, pre-recorded or computer-generated voice calls or voicemails, mobile push notifications through a mobile application, etc. The information included in the alerts and the recipients of the alerts may be based on a determined severity of the threat posed to occupants of the vehicle. In particular embodiments, the alerts may include a location of the vehicle, obtained from a GPS receiver 49, for example. Computer 20 may use any suitable means of wireless communications, such as cellular, satellite, Wi-Fi, etc.

Figure 3:
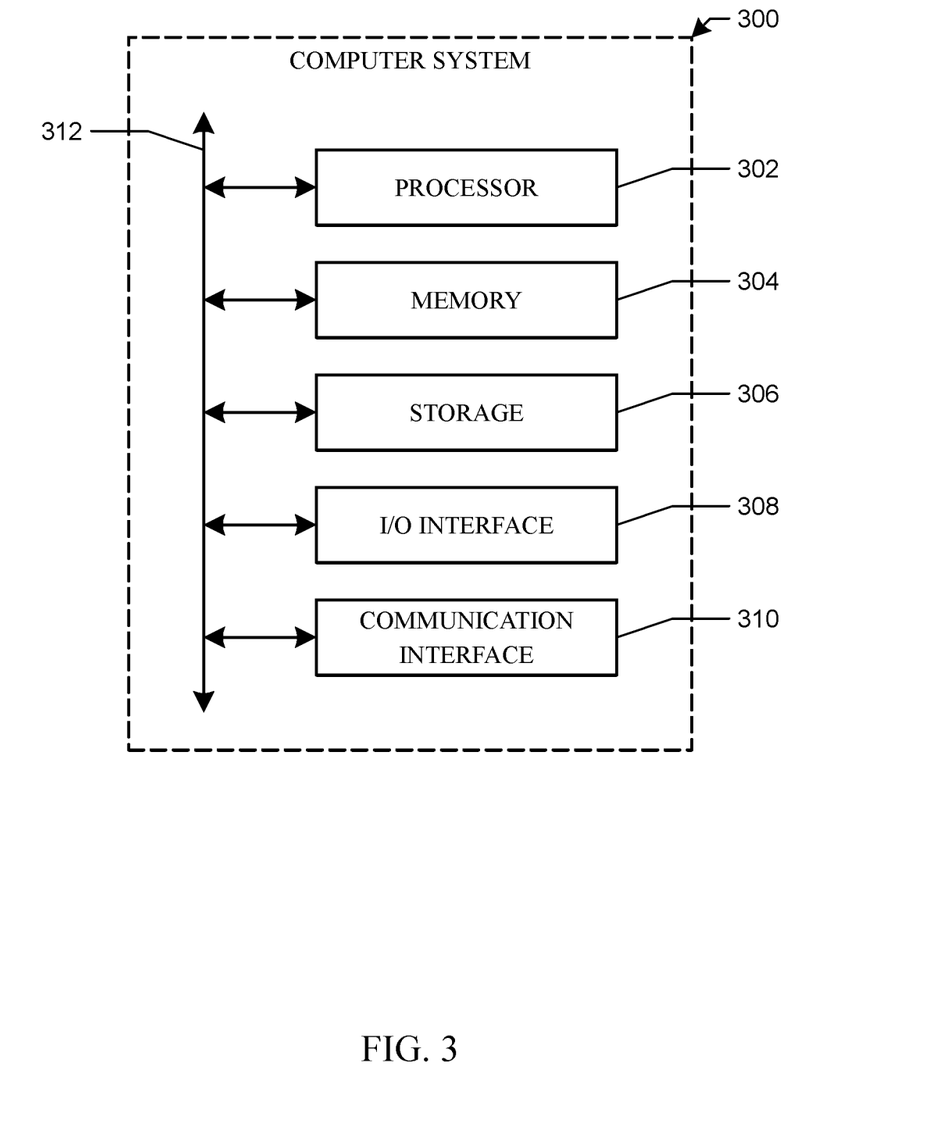
FIG. 3 is an example computer system useful for implementing various embodiments.

FIG. 3 illustrates an example computer system 300. In particular embodiments, one or more computer systems 300 perform one or more steps of one or more methods described or illustrated herein. In particular embodiments, one or more computer systems 300 provide functionality described or illustrated herein. In particular embodiments, software running on one or more computer systems 300 performs one or more steps of one or more methods described or illustrated herein or provides functionality described or illustrated herein. Particular embodiments include one or more portions of one or more computer systems 300. Herein, reference to a computer system may encompass a computing device, and vice versa, where appropriate. Moreover, reference to a computer system may encompass one or more computer systems, where appropriate.

This disclosure contemplates any suitable number of computer systems 300. This disclosure contemplates computer system 300 taking any suitable physical form. As example, computer system 300 may be an embedded computer system, a desktop computer system, a laptop or notebook computer system, a mainframe, a mobile telephone, a personal digital assistant (PDA), a server, a tablet computer system, or a combination of two or more of these. Where appropriate, computer system 300 may include one or more computer systems 300; be unitary or distributed; span multiple locations; span multiple machines; span multiple data centers; or reside in a cloud, which may include one or more cloud components in one or more networks. Where appropriate, one or more computer systems 300 may perform without substantial spatial or temporal limitation one or more steps of one or more methods described or illustrated herein. As an example, one or more computer systems 300 may perform in real time or in batch mode one or more steps of one or more methods described or illustrated herein. One or more computer systems 300 may perform at different times or at different locations one or more steps of one or more methods described or illustrated herein, where appropriate.

In particular embodiments, computer system 300 includes a processor 302, memory 304, storage 306, an input/output (I/O) interface 308, a communication interface 310, and a bus 312. Although this disclosure describes and illustrates a particular computer system having a particular number of particular components in a particular arrangement, this disclosure contemplates any suitable computer system having any suitable number of any suitable components in any suitable arrangement.

In particular embodiments, processor 302 includes hardware for executing instructions, such as those making up a computer program. As an example, to execute instructions, processor 302 may retrieve (or fetch) the instructions from an internal register, an internal cache, memory 304, or storage 306; decode and execute them; and then write one or more results to an internal register, an internal cache, memory 304, or storage 306. In particular embodiments, processor 302 may include one or more internal caches for data, instructions, or addresses. This disclosure contemplates processor 302 including any suitable number of any suitable internal caches, where appropriate. In particular embodiments, processor 302 may include one or more internal registers for data, instructions, or addresses. This disclosure contemplates processor 302 including any suitable number of any suitable internal registers, where appropriate. Where appropriate, processor 302 may include one or more arithmetic logic units (ALUs); be a multi-core processor; or include one or more processors 302. Although this disclosure describes and illustrates a particular processor, this disclosure contemplates any suitable processor.

In particular embodiments, memory 304 includes main memory for storing instructions for processor 302 to execute or data for processor 302 to operate on. As an example, computer system 300 may load instructions from storage 306 or another source (such as, for example, another computer system 300) to memory 304. Processor 302 may then load the instructions from memory 304 to an internal register or internal cache. To execute the instructions, processor 302 may retrieve the instructions from the internal register or internal cache and decode them. During or after execution of the instructions, processor 302 may write one or more results (which may be intermediate or final results) to the internal register or internal cache. Processor 302 may then write one or more of those results to memory 304. In particular embodiments, processor 302 executes only instructions in one or more internal registers or internal caches or in memory 304 (as opposed to storage 306 or elsewhere) and operates only on data in one or more internal registers or internal caches or in memory 304 (as opposed to storage 306 or elsewhere). One or more memory buses (which may each include an address bus and a data bus) may couple processor 302 to memory 304. Bus 312 may include one or more memory buses, as described below. In particular embodiments, memory 304 includes random access memory (RAM). This RAM may be volatile memory, where appropriate Memory 304 may include one or more memories 304, where appropriate. Although this disclosure describes and illustrates particular memory, this disclosure contemplates any suitable memory.

In particular embodiments, storage 306 includes mass storage for data or instructions. As an example, storage 306 may include a hard disk drive (HDD), a floppy disk drive, flash memory, an optical disc, a magneto-optical disc, magnetic tape, or a Universal Serial Bus (USB) drive or a combination of two or more of these. Storage 306 may include removable or non-removable (or fixed) media, where appropriate. Storage 306 may be internal or external to computer system 300, where appropriate. In particular embodiments, storage 306 is non-volatile, solid-state memory. In particular embodiments, storage 306 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 306 taking any suitable physical form. Storage 306 may include one or more storage control units facilitating communication between processor 302 and storage 306, where appropriate. Where appropriate, storage 306 may include one or more storages 306. Although this disclosure describes and illustrates particular storage, this disclosure contemplates any suitable storage.

In particular embodiments, I/O interface 308 includes hardware, software, or both, providing one or more interfaces for communication between computer system 300 and one or more I/O devices. Computer system 300 may include one or more of these I/O devices, where appropriate. One or more of these I/O devices may enable communication between a person and computer system 300. As an example, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 308 for them. Where appropriate, I/O interface 308 may include one or more device or software drivers enabling processor 302 to drive one or more of these I/O devices. I/O interface 308 may include one or more I/O interfaces 308, where appropriate. Although this disclosure describes and illustrates a particular I/O interface, this disclosure contemplates any suitable I/O interface.

In particular embodiments, communication interface 310 includes hardware, software, or both providing one or more interfaces for communication (such as, for example, packet-based communication) between computer system 300 and one or more other computer systems 300 or one or more networks. As an example, communication interface 310 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 310 for it. As an example, computer system 300 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 300 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), satellite, or other suitable wireless network or a combination of two or more of these. Computer system 300 may include any suitable communication interface 310 for any of these networks, where appropriate. Communication interface 310 may include one or more communication interfaces 310, where appropriate. Although this disclosure describes and illustrates a particular communication interface, this disclosure contemplates any suitable communication interface.

In particular embodiments, bus 312 includes hardware, software, or both coupling components of computer system 300 to each other. As an example, bus 312 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 312 may include one or more buses 312, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A computer-implemented method performed by at least one processor operatively coupled to a memory storing instructions which, when executed by the processor, cause the processor and the memory when comprised in a vehicle to perform method steps in the vehicle, including:
    receiving input from a graphical user interface on which a user enters desired configuration information;
    configuring a system for detection and prevention of unattended vehicle deaths to operate in accordance with the entered configuration information;
    receiving one or more signals from one or more presence sensors in a vehicle;
    analyzing the one or more signals from the one or more presence sensors to detect a presence of a person or an animal inside of the vehicle;
    receiving one or more signals from one or more environment sensors on the vehicle;
    analyzing the one or more signals from the one or more environment sensors to detect a dangerous environmental condition;
    determining that both the presence of a person or animal has been detected inside the vehicle and a dangerous environmental condition has been detected;
    determining, by the at least one processor, if the vehicle is in a confined space having low ventilation based on a concentration of carbon monoxide gas in the air prior to performing a mitigating action comprising the steps of:
        turning on, by the at least one processor, an ignition of the vehicle and orienting at least a portion of a window of the vehicle in an open position;
        measuring, by a carbon monoxide gas sensor, the concentration of the carbon monoxide gas within the vehicle;
        responsive to detecting the concentration of the carbon monoxide gas having a concentration greater than a predetermined threshold, turning off, by the at least one processor, the ignition of the vehicle; and
        responsive to detecting the concentration of the carbon monoxide gas responsive to detecting the concentration of the carbon monoxide gas having a concentration lower than a predetermined threshold, determining, by the at least one processor, that the vehicle is not in the confined space;
    responsive to determining that the vehicle is not in the confined space, activating one or more vehicle systems that mitigate the dangerous environmental condition; and
    sending an alert to one or more predetermined recipients.

2. The method of claim 1, wherein the one or more vehicle systems that mitigate the dangerous environmental condition comprise at least one of a ventilation system, air conditioning system, heating system, or window control system.

3. The method of claim 1, wherein sending the alert comprises sending a message including the vehicle's location over a wireless communications channel.

4. A system for prevention of unattended vehicle deaths, comprising:
    a vehicle comprising:
        one or more presence sensors;
        one or more environment sensors;
        a memory; and
        at least one processor coupled to the memory, the one or more presence sensors, the one or more environment sensors, and a screen that displays a graphical user interface, the processor executing computer readable instructions stored in the memory to cause the system to:
receive input from the graphical user interface on which a user enters desired configuration information;
configure the system for detection and prevention of unattended vehicle deaths to operate in accordance with the entered configuration information;
receive one or more signals from the one or more presence sensors in the vehicle;
analyze the one or more signals from the one or more presence sensors to detect a presence of a person or an animal inside of the vehicle;
receive one or more signals from one or more environment sensors on the vehicle;
analyze the one or more signals from the one or more environment sensors to detect a dangerous environmental condition;
in the case the presence of a person or animal has been detected inside the vehicle and a dangerous environmental condition has been detected:
determining, by the computer, if the vehicle is in a confined space having low ventilation based on a concentration of carbon monoxide gas in the air prior to performing a mitigating action comprising the steps of:
turning on, by the computer, an ignition of the vehicle and orienting at least a portion of a window of the vehicle in an open position;
measuring, by a carbon monoxide gas sensor, the concentration of the carbon monoxide gas within the vehicle;
responsive to detecting the concentration of the carbon monoxide gas having a concentration greater than a predetermined threshold, turning off, by the computer, the ignition of the vehicle; and
responsive to detecting the concentration of the carbon monoxide gas having a concentration lower than a predetermined threshold, determining, by the computer, that the vehicle is not in the confined space;
responsive to determining that the vehicle is not in the confined space, activating one or more vehicle systems that mitigate the dangerous environmental condition; and
send an alert to one or more predetermined recipients.

5. A tangible computer-readable device having instructions stored thereon that, when executed by at least one computing device in a vehicle, causes the at least one computing device to perform operations in the vehicle when the vehicle comprises components of a system for prevention of unattended vehicle deaths, the operations comprising:
receiving input from a graphical user interface of the vehicle on which a user enters desired configuration information;
configuring a system of the vehicle for detection and prevention of unattended vehicle deaths to operate in accordance with the entered configuration information;
receiving one or more signals from one or more presence sensors of the vehicle;
analyzing, by a processor of the vehicle, the one or more signals from the one or more presence sensors to detect a presence of a person or an animal inside of the vehicle;
receiving, in the vehicle, one or more signals from one or more environment sensors on the vehicle;
analyzing, by a processor of the vehicle, the one or more signals from the one or more environment sensors to detect a dangerous environmental condition;
in the case both the presence of a person or animal has been detected inside the vehicle and a dangerous environmental condition has been detected:
determining, by the computer, if the vehicle is in a confined space having low ventilation based on a concentration of carbon monoxide gas in the air prior to performing a mitigating action comprising the steps of:
turning on, by the computer, an ignition of the vehicle and orienting at least a portion of a window of the vehicle in an open position;
measuring, by a carbon monoxide gas sensor, the concentration of the carbon monoxide gas within the vehicle;
responsive to detecting the concentration of the carbon monoxide gas having a concentration greater than a predetermined threshold, turning off, by the computer, the ignition of the vehicle; and
responsive to detecting the concentration of the carbon monoxide responsive to detecting the concentration of the carbon monoxide gas having a concentration lower than a predetermined threshold, determining, by the computer, that the vehicle is not in the confined space;
responsive to determining that the vehicle is not in the confined space, activating one or more vehicle systems that mitigate the dangerous environmental condition; and
sending an alert to one or more predetermined recipients.

* * * * *